United States Patent [19]

Hammerman et al.

[11] Patent Number: 5,569,791
[45] Date of Patent: Oct. 29, 1996

[54] PRODUCTION OF PHENOL FROM A HYDROCARBON FEEDSTOCK

[75] Inventors: John I. Hammerman, Arlington Heights; Peter R. Pujado, Palatine, both of Ill.

[73] Assignee: UOP, Des Plaines, Ill.

[21] Appl. No.: 428,602

[22] Filed: Apr. 25, 1995

[51] Int. Cl.$^6$ ..................................................... C07C 37/00
[52] U.S. Cl. ........................................................ 568/803
[58] Field of Search ............................................. 568/803

[56] References Cited

U.S. PATENT DOCUMENTS

| | | | |
|---|---|---|---|
| 3,453,332 | 7/1969 | Vesely et al. | 260/613 |
| 5,211,837 | 5/1993 | Russ et al. | 208/65 |
| 5,233,097 | 8/1993 | Nemeth et al. | 568/803 |
| 5,258,563 | 11/1993 | Gosling et al. | 585/322 |

*Primary Examiner*—Samuel Barts
*Attorney, Agent, or Firm*—Thomas K. McBride; John F. Spears, Jr.; Richard E. Conser

[57] ABSTRACT

Phenol is produced from a hydrocarbon feedstock using a process combination offering unexpected synergy. Benzene is produced from the hydrocarbon feedstock using a highly selective aromatization catalyst which provides substantial quantities of high-purity hydrogen. The hydrogen is converted to hydrogen peroxide, which in turn is used to convert the benzene to phenol in high yield.

21 Claims, 1 Drawing Sheet

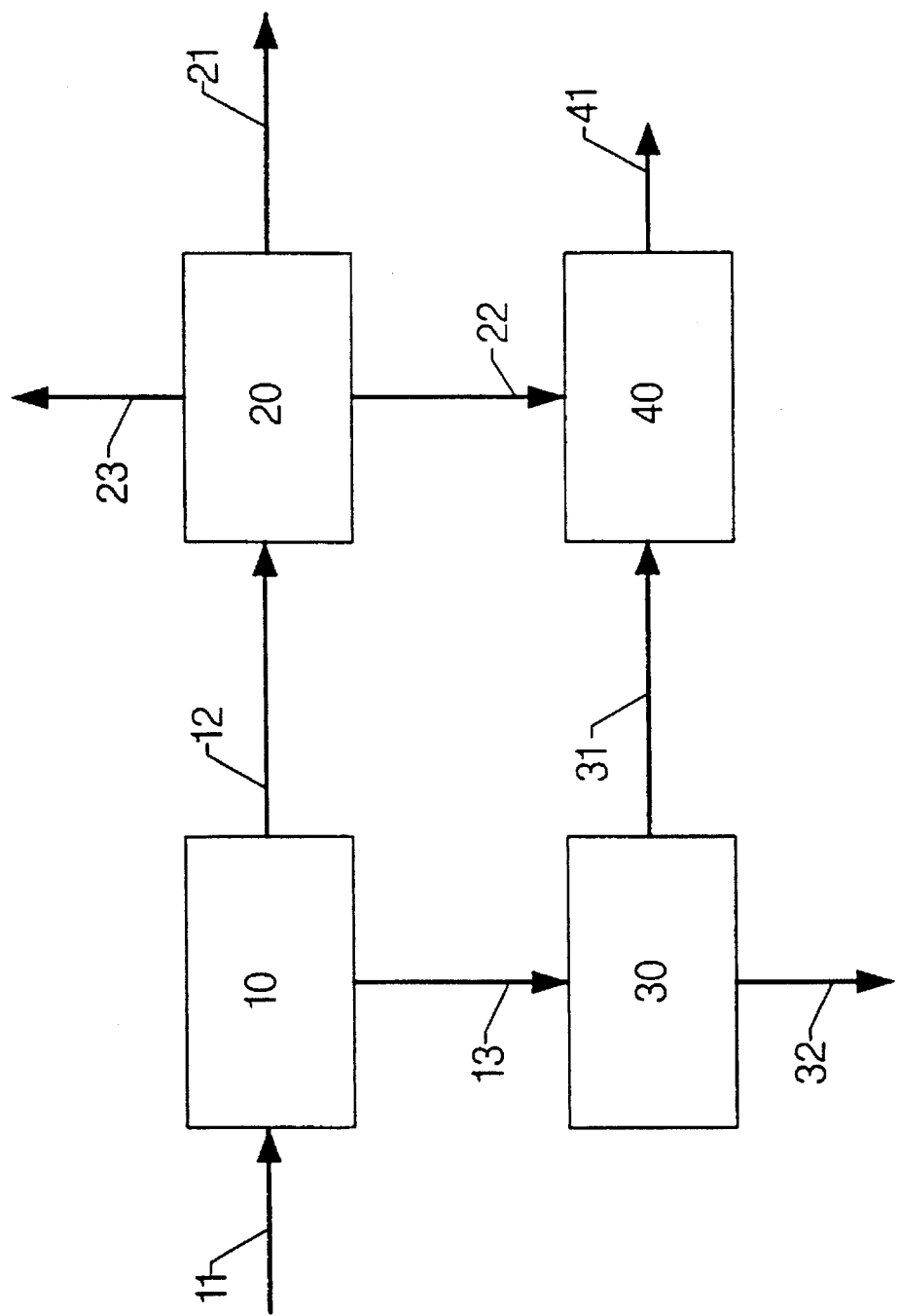

5,569,791

PRODUCTION OF PHENOL FROM A HYDROCARBON FEEDSTOCK

FIELD OF THE INVENTION

This invention relates to a process for the oxidation of hydrocarbons, and more specifically for the production of phenol from a hydrocarbon feedstock.

BACKGROUND OF THE INVENTION

Phenol is one of the most important chemical intermediates, reflecting primarily its high-volume use in resin manufacture. Principal end products comprise phenolic resins, principally phenol-formaldehyde resins used in the construction, appliance and automotive industries, and Bisphenol A for epoxy and polycarbonate resins. A significant proportion of the phenol produced is used to produce alkylphenols, which are converted to nonionic surfactants, resins and modifiers, agrochemicals and pharmaceuticals.

The dominant process for production of phenol proceeds via cumene and cumene hydroperoxide. Benzene and propylene are alkylated to obtain cumene, which in turn is oxidized to form cumene hydroperoxide. The hydroperoxide is cleaved using an acid catalyst to form phenol and acetone. The economics of phenol production by the cumene route are highly favorable compared to older processes, leading to the dominance of this route. Essentially one mole of acetone is produced for each mole of phenol, however, leading to an undesirable rigidity in product structure.

Phenol via toluene oxidation was developed by Dow, DSM and others to overcome the byproduct issue associated with the cumene route, but the inherent yield loss and expensive materials of construction prevented this route from making strong inroads. Older processes such as sulfonation, chlorobenzene, and the Raschig Hooker process converted benzene without substantial hydrocarbon byproducts but were burdened by such disadvantages of high chemical and energy consumption, corrosion, and the need for catalyst regeneration. The Scientific Design cyclohexanone/cyclohexanol route was not economic for phenol alone due to a phenol/cyclohexanone azeotrope. A problem facing workers in the field of phenol technology, therefore, is to develop an economically attractive route for phenol production which avoids the byproduct, corrosion and operating-cost disadvantages of earlier processes.

Nemeth et al. teach a process for the direct hydroxylation of aromatic compounds using hydrogen peroxide in U.S. Pat. No. 5,233,097. Using a titanoaluminosilicate molecular sieve, the process achieves high product selectivity using relatively dilute hydrogen peroxide solutions; the state of the art based on titanosilicate catalysts and types of hydrogen peroxide solutions is discussed extensively. An earlier process for the direct hydroxylation of aromatics with hydrogen peroxide using a hydrogen fluoride-carbon dioxide complex is disclosed in U.S. Pat. No. 3,453,332 (Vesely et al.).

Production of the benzene feedstock for direct oxidation has not been related to a phenol-production scheme, but a variety of processes are available to obtain benzene. In addition to conventional catalytic reforming. U.S. Pat. No. 5,211,837 teaches processing with a sulfur-sensitive L-zeolite catalyst that favors benzene production from lighter naphtha feedstocks. U.S. Pat. No. 5,258,563 discloses production of benzene in high yields from light aliphatic hydrocarbons.

Phenol from cumene nevertheless remains the process of choice for commercial installations in spite of the issue of byproduct acetone; direct conversion of benzene to phenol has not become economically attractive based on the teachings of the art.

SUMMARY OF THE INVENTION

The objective of this invention is to convert a mixed hydrocarbon stream to achieve a high yield of a hydroxylaromatic product. A related objective is to provide a direct-oxidation process for the production of phenol that is competitive with the conventional route via cumene hydroperoxide.

The invention is based on the discovery that a processing scheme including production of benzene and hydrogen which in turn are used to produce phenol via hydrogen peroxide provides synergy resulting in surprisingly favorable economics.

A broad embodiment of the present invention is a process combination comprising aromatization of a hydrocarbon feedstock to produce an aromatic product and hydrogen, use of the hydrogen to produce a peroxide, and use of the peroxide to hydroxylate the aromatic product to a hydroxylaromatic product. A more specific embodiment is a process combination comprising aromatization of a hydrocarbon feedstock to produce benzene and hydrogen, use of the hydrogen to produce hydrogen peroxide, and use of the peroxide to hydroxylate the benzene to phenol.

A favored process for production of benzene and hydrogen is aromatization of a naphtha feedstock using a catalyst containing a platinum-group metal and nonacidic L-zeolite. Alternatively, light aliphatic hydrocarbons are converted to benzene and hydrogen using a gallium-containing zeolitic catalyst. Hydrogen from the aromatization process is converted to hydrogen peroxide, optimally via anthrahydroquinone autoxidation.

Preferably benzene is hydroxylated to phenol using hydrogen peroxide at moderate temperatures with good utilization of the hydrogen peroxide and good selectivity in the presence of a titanoaluminosilicate catalyst where the titanium, aluminum, and silicon are present as framework tetrahedral oxide units.

Other embodiments will become apparent from the ensuing detailed description.

BRIEF DESCRIPTION OF THE DRAWING

The drawing is a simplified process flow diagram showing the arrangement of the principal process units comprising the invention.

DETAILED DESCRIPTION OF THE INVENTION

The present invention comprises a process combination which includes the following steps:

aromatization of a hydrocarbon feedstock to produce an aromatics-rich effluent, preferably comprising benzene, and hydrogen;

separation of the aromatics-rich effluent to obtain an aromatic compound which preferably comprises benzene;

use of the hydrogen to produce a peroxide, which preferably comprises hydrogen peroxide; and, use of the peroxide to hydroxylate the aromatic compound to obtain a hydroxylaromatic product which preferably comprises phenol. The arrangement of the principal process units comprising the invention is shown in the drawing.

An aromatization zone 10 processes a hydrocarbon feedstock introduced via line 11, which favorably is a gasoline-range naphtha feedstock, to produce an aromatics-rich effluent recovered via line 12. A hydrogen concentrate is recovered as a gaseous byproduct in line 13.

The aromatics-rich effluent is processed in aromatics-separation zone 20, preferably via extraction, to separate an aromatic concentrate from a nonaromatics stream comprising other hydrocarbons such as paraffins, olefins and naphthenes; the non-aromatics stream is removed from the separation zone via line 21. The aromatic concentrate recovered in the separation zone may be further partitioned, for example by fractional distillation, to obtain an aromatic compound for hydroxylation as described hereinbelow. The aromatic compound is recovered via line 22, and an aromatic byproduct from the partitioning of the aromatic concentrate may be removed from the separation zone in line 23. It is within the scope of the invention that the aromatic byproduct may be converted in other processing steps not shown in the drawing to additional aromatic compound; e.g., toluene byproduct may be processed by dealkylation or disproportionation to obtain additional benzene for hydroxylation.

The hydrogen concentrate (optionally following upgrading to obtain a purified hydrogen stream) is processed in a peroxidation zone 30 to obtain a peroxide, preferably hydrogen peroxide, for hydroxylating the aromatic compound. The peroxide is recovered via line 31, and a gaseous byproduct is removed in line 32.

The aromatic compound and peroxide are directed to a hydroxylation zone 40 in which they are converted into a hydroxylaromatic product recovered via line 41. Preferably, phenol is produced from benzene and hydrogen peroxide.

The hydrocarbon feedstock comprises paraffins and naphthenes, and may comprise aromatics and small amounts of olefins, usually boiling within the gasoline range or lighter. Feedstocks which may be utilized include straight-run naphthas, natural gasoline, synthetic naphthas, thermal gasoline, catalytically cracked gasoline, partially reformed naphthas or raffinates from extraction of aromatics. The distillation range may be that of a full-range naphtha, having an initial boiling point typically from 40°–80° C. and a final boiling point of from about 160°–210° C., or it may represent a narrower range with a lower final boiling point. Paraffinic feedstocks, such as naphthas from Middle East crudes having a final boiling point of from about 100°–175° C. are advantageously processed since the process combination effectively dehydrocyclizes paraffins to aromatics. The especially preferred boiling range encompasses $C_6$–$C_8$ naphtha, i.e., an initial boiling point of about 60°–80° C. and a final boiling point of about 100°–160° C., which yield benzene, toluene and xylenes ("BTX") suitable for production of phenol, cresols and xylenols by the present process. Raffinates from aromatics extraction, containing principally low-value $C_6$–$C_8$ paraffins which can be converted to BTX via the present process combination, are favorable alternative or supplementary hydrocarbon feedstocks. The nonaromatics stream from the aromatics-separation zone is one such raffinate, and usefully comprises a portion of the hydrocarbon feedstock.

The hydrocarbon feedstock usually contains small amounts of sulfur compounds, amounting generally to less than 10 mass parts per million (ppm) on an elemental basis. Preferably the hydrocarbon feedstock has been prepared from a contaminated feedstock by a conventional pretreating step such as hydrotreating, hydrorefining or hydrodesulfurization to convert such contaminants as sulfurous, nitrogenous and oxygenated compounds to $H_2S$, $NH_3$ and $H_2O$, respectively, which can be separated from the hydrocarbons by fractionation. This conversion preferably will employ a catalyst known to the art comprising an inorganic oxide support and metals selected from Groups VIB(6) and VIII(9–10) of the Periodic Table. See Cotton and Wilkinson, *Advanced Inorganic Chemistry*, John Wiley & Sons (Fifth Edition, 1988).

Alternatively or in addition to the conventional hydrotreating, the pretreating step may comprise contact with agents capable of removing sulfurous and other contaminants. These agents may include but are not limited to zinc oxide, iron sponge, high-surface-area sodium, high-surface-area alumina, activated carbons and molecular sieves; excellent results are obtained with a nickel-on-alumina removal agent. Preferably, the pretreating step will provide the aromatization catalyst with a hydrocarbon feedstock having low sulfur levels disclosed in the prior art as desirable reforming feedstocks, e.g., 1 ppm to 0.1 ppm (100 ppb). The pretreating step may achieve very low sulfur levels in the hydrocarbon feedstock by combining a relatively sulfur-tolerant aromatization catalyst with a sulfur sorbent. The sulfur-tolerant aromatization catalyst contacts the contaminated feedstock to convert most of the sulfur compounds to yield an $H_2S$-containing effluent. The $H_2S$-containing effluent contacts the sulfur sorbent, which advantageously is a zinc oxide or manganese oxide, to remove $H_2S$. Sulfur levels well below 0.1 mass ppm may be achieved thereby. It is within the ambit of the present invention that the pretreating step be included in the present reforming process.

It is within the scope of the invention that the aromatization zone is divided into a first aromatization zone containing a catalyst system comprising a physical mixture of a aromatization catalyst and a sulfur sorbent comprising a manganese component, followed by a second aromatization zone containing only the aromatization catalyst. The co-action of the catalyst and sorbent provides excellent results in achieving favorable yields with high catalyst utilization in a dehydrocyclization operation using a sulfur-sensitive catalyst.

The hydrocarbon feedstock contacts the aromatization catalyst in the aromatization zone to convert paraffins and naphthenes to aromatics and obtain an aromatics-rich effluent. Reforming conditions used in the aromatization zone of the present invention include a pressure of from about 100 kPa to 7 MPa (absolute), with the preferred range being from 100 kPa to 2 MPa and a pressure of about 1 MPa or below being especially preferred. Free hydrogen is supplied to the aromatization zone preferably by separation and recycle from aromatization products in an amount sufficient to correspond to a ratio of from about 0.1 to 10 moles of hydrogen per mole of hydrocarbon feedstock. By "free hydrogen" is meant molecular $H_2$, not combined in hydrocarbons or other compounds. The volume of the contained aromatization catalyst corresponds to a liquid hourly space velocity of from about 0.5 to 40 $hr^{-1}$. The reforming conditions comprise a temperature, defined as the maximum temperature of the combined hydrocarbon feedstock, free hydrogen, and any components accompanying the free hydrogen, generally in the range of 260° to 600° C.

In a variant of the principal embodiment, the aromatization comprises dehydrocyclodimerization of $C_2$–$C_6$ aliphatic hydrocarbons such as isobutane, normal butane, isobutene, normal butene, propane and propylene. Diluents such as nitrogen, helium, neon and argon also may be included in the feed stream. Reforming conditions for dehydrocyclodimerization of $C_2$–$C_6$ aliphatic hydrocarbons to aromatics include a temperature from about 350° C. to about 600° C. and a liquid hourly space velocity from about 0.2 to about $hr^{-1}$. As the average carbon number of the feed decreases, a temperature in the lower portion of the temperature range is required for optimum performance.

The catalyst for the dehydrocyclodimerization embodiment of the aromatization comprises a zeolite, phosphorus-modified alumina (hereinafter aluminum phosphate) binder and a gallium component. These catalysts are well known in the art and their preparation is also well known as shown by U.S. Pat. No. 4,629,717 which is incorporated by reference. Suitable zeolites have a Si:Al ratio greater than about 10, preferably greater than 20, and a pore diameter of about 5 to 6 Angstroms. Specific examples of zeolites which can be used are the ZSM family including ZSM-5, ZSM-8, ZSM-11, ZSM-12 and ZSM-35. The amount of zeolite present in the catalyst can vary considerably but usually is present in an amount from about 30 to about 90 mass-% and preferably from about 50 to about 70 mass-of the catalyst.

The aluminum phosphate component is prepared by combining phosphorus with the alumina in a proportion of from about 1:1 to 1:100 on an elemental basis by any acceptable manner known in the art. One preferred method of preparing the aluminum phosphate is that described in U.S. Pat. No. 4,629,717 and involves the gelation of a hydrosol of alumina which contains a phosphorus compound using the well-known oil drop method. The zeolite and aluminum phosphate binder are mixed and formed into particles by means well known in the art such as gelation, pilling, nodulizing, marumerizing, spray drying, extrusion or any combination of these techniques, and preferably are combined with the aluminum phosphate hydrosol before gelling this mixture. Usually a gelling agent such as hexamethylenetetramine and/or urea is added to the mixture, which then is dispersed into an oil bath or tower which has been heated to elevated temperatures to effect gelation with the formation of spheroidal particles which subsequently are calcined. The proportion of aluminum phosphate present (as the oxide) in the catalyst can range from about 10 to about 70 mass-% and preferably from about 30 to about 50 mass-%.

The gallium component may be deposited onto the support in any suitable manner known to the art which results in a uniform dispersion of from about 0.1 to about 5 mass-% of the finished catalyst as gallium on an elemental basis. Usually a gallium salt is impregnated onto the support particles by any technique well known in the art such as dipping the catalyst into a solution of the metal compound or spraying the solution onto the support. One preferred method of preparation involves immersing and tumbling the catalyst particles in an impregnating solution contained in a rotary dryer and applying steam to the dryer jacket. Dry particles are heated under a hydrogen atmosphere at a temperature of about 500 to about 700° C. for a time of about 1 to about 15 hours; the reduction and dispersion can be done in situ in the actual reactor vessel. It is preferred that they be treated with an aqueous solution of a weakly acidic ammonium salt or a dilute acid solution, preferably comprising ammonium nitrate, to minimize the deactivation caused by exposure to hydrogen.

Usually the aromatization zone comprises multiple reactors containing the aromatization catalyst. Since a major reaction occurring in the aromatization zone is the dehydrocyclization of paraffins to aromatics along with the usual dehydrogenation of naphthenes, the resulting endothermic heat of reaction may cool the reactants below the temperature at which reforming takes place before sufficient dehydrocyclization has occurred. Naphthenes generally are dehydrogenated to a large extent in the first reactors of the aromatization zone with a concomitant large decline in temperature across the catalyst bed due to the endothermic heat of reaction. Therefore, this zone usually comprises two or more reactors with interheating-between reactors to raise the temperature and maintain dehydrocyclization conditions. Initial reaction temperature generally is slowly increased during each period of operation to compensate for the inevitable catalyst deactivation. The temperature to the reactors of the aromatization zones may be staggered, i.e., differ between reactors, in order to achieve product objectives.

Contacting within the aromatization zone may be effected using the catalyst in a fixed-bed system, a moving-bed system, a fluidized-bed system, or in a batch-type operation; fixed-bed and moving-bed systems have proven particularly useful in commercial operations, with continuous catalyst regeneration preferably associated with the moving-bed system. The reactants may be contacted with the catalyst in either upward, downward, or radial-flow fashion, with radial-flow contact being favored in low-pressure aromatization operations to reduce pressure drop. The reactants may be in the liquid phase, a mixed liquid-vapor phase, or a vapor phase when contacting the catalyst bed. The aromatization zone may be in a single reactor or in two or more separate reactors with suitable means therebetween to ensure that the desired reforming temperature is maintained at the entrance to each zone. Two or more reactors in sequence are preferred to enable improved reforming through control of individual reactor temperatures.

Reforming operating conditions include a pressure of from about 100 kPa to 4 MPa (absolute), with the preferred range being from about 100 kPa to 2 MPa and a pressure of below about 1000 kPa being especially preferred. Hydrogen is supplied to the reforming zone in an amount sufficient to correspond to a ratio of from about 0.1 to 10 moles of hydrogen per mole of hydrocarbon feedstock. The operating temperature generally is in the range of about 260° to 560° C. The volume of the contained aromatization catalyst corresponds to a liquid hourly space velocity of from about 0.5 to 40 $hr^{-1}$.

The aromatization catalyst comprises a supported platinum-group metal component, with a platinum component being preferred. The platinum-group metal may exist within the catalyst as a compound, in chemical combination with one or more other ingredients of the catalytic composite, or as an elemental metal; best results are obtained when substantially all of the platinum exists in the catalytic composite in a reduced state. The concentration of the platinum-group metal in the finished catalyst preferably is from about 0.01 to 0.2 mass-% on an elemental basis. The catalyst may contain other metal components known to modify the effect of the preferred platinum component, including Group IVA (14) metals, other Group VIII (8–10) metals, rhenium, indium, gallium, zinc, uranium, dysprosium, thallium and mixtures thereof in an amount of from about 0.01 to 0.5 mass-%, on an elemental basis, of the catalyst.

The aromatization catalyst comprises a refractory support which should be a porous, adsorptive, high-surface-area material which is uniform in composition. Preferably the support comprises refractory inorganic oxides such as alumina, silica, titania, magnesia, zirconia, chromia, thoria, boria or mixtures thereof, especially alumina with gamma- or eta-alumina being particularly preferred and best results being obtained with "Ziegler alumina" as described hereinbefore and in the references. Optional ingredients are crystalline zeolitic aluminosilicates, either naturally occurring or synthetically prepared such as FAU, MEL, MFI, MOR, MTW (IUPAC Commission on Zeolite Nomenclature), and non-zeolitic molecular sieves such as the aluminophosphates of U.S. Pat. No. 4,310,440 or the silicoaluminophosphates of U.S. Pat. No. 4,440,871 (incorporated by reference). Further details of the preparation and activation of embodiments of the above aromatization catalyst are disclosed in U.S. Pat. No. 4,677,094 (Moser et al.), which is incorporated into this specification by reference thereto.

In an especially preferred embodiment, the aromatization catalyst comprises a large-pore molecular sieve. The term "large-pore molecular sieve" is defined as a molecular sieve having an effective pore diameter of about 7 angstroms or larger. Examples of large-pore molecular sieves which might be incorporated into the present catalyst include LTL, FAU, AFI, MAZ, and zeolite-beta, with a nonacidic L-zeolite (LTL) being especially preferred. An alkali-metal component, preferably comprising potassium, and a platinum-group metal component, preferably comprising platinum, are essential constituents of the especially preferred aromatization catalyst. The alkali metal optimally will occupy essentially all of the cationic exchangeable sites of the nonacidic L-zeolite. Further details of the preparation and activation of embodiments of the alternative aromatization catalyst are disclosed, e.g., in U.S. Pat. Nos. 4,619,906 (Lambert et al) and 4,822,762 (Ellig et al.), which are incorporated into this specification by reference thereto.

The aromatization zone produces an aromatics-rich effluent, with the aromatics content of the $C_5+$ portion increased by at least 5 mass % relative to the aromatics content of the hydrocarbon feedstock. The composition of the aromatics will depend principally on the feedstock composition and operating conditions, and generally will be within the range of $C_6$–$C_{12}$. Benzene, toluene and/or $C_8$ aromatics usually are the preferred aromatics produced from the favored light naphtha and raffinate feedstocks, with benzene being particularly preferred for subsequent hydroxylation to phenol.

A hydrogen concentrate, or hydrogen-rich gas is a byproduct of the aromatization reaction. This gas stream is divided as a net stream from aromatization recycle gas which is taken from a separator which processes reactor effluent after cooling. The hydrogen concentrate contains at least 60 mole-%, generally 80 mole-% or more, and often 90 mole-% or more of hydrogen with the balance being principally methane and heavier hydrocarbons. It is within the scope of the invention that the hydrogen concentrate is upgraded to a purified hydrogen stream by any means known in the art by separation from byproduct hydrocarbons produced in the aromatization reaction. A purified hydrogen stream has a hydrogen content of at least about 90 mole-%, preferably 99 mole-% or more, and more preferably at least about 99.9 mole-% hydrogen. Suitable upgrading methods include but are not limited to adsorption, especially pressure-swing adsorption as taught in U.S. Pat. No. 5,177,293; absorption, preferably absorbing hydrocarbons from the hydrogen concentrate using a medium which is less volatile than the hydrocarbons; cooling, especially cryogenic separation; and membrane separation.

The aromatization zone generally comprises a stabilization section, usually comprising one or more fractional distillation columns having associated appurtenances and separating lighter components from the reformate product. In addition, the aromatics-rich effluent may be separated into two or more fractions to provide a suitable fraction to recover an aromatic compound for subsequent hydroxylation as disclosed hereinbelow.

An aromatics concentrate is recovered from the aromatics-rich effluent as feed to hydroxylation in an aromatics-recovery zone by any method that provides a product of suitable purity. Suitable methods include selective adsorption with molecular sieves, and, preferably, solvent extraction. Solvent extraction typically comprises contacting the heavy reformate in an extraction zone with an aromatic-extraction solvent which selectively extracts aromatic hydrocarbons. The aromatic hydrocarbons generally are recovered as extract from the solvent phase by one or more distillation steps, and the raffinate from extraction typically is purified by water washing. Solvent extraction normally will recover from about 90 to 100% of the aromatics from the aromatics-rich effluent into the extract and reject from about 95 to 100% of the paraffins from the aromatics-rich effluent into the raffinate.

Solvent compositions are selected from the classes which have high selectivity for aromatic hydrocarbons and are known to those of ordinary skill in the hydrocarbon-processing art. These generally comprise one or more organic compounds containing in their molecule at least one polar group, such as a hydroxyl-, amino-, cyano-, carboxyl- or nitro- radical, preferably selected from the aliphatic and cyclic alcohols, cyclic monomeric sulfones, glycols and glycol ethers, glycol esters and glycol ether esters. The mono- and poly-alkylene glycols in which the alkylene group contains from 2 to 4 carbon atoms constitute a satisfactory class of organic solvents useful in admixture with water as a solvent composition for use in the present invention. Other suitable solvents include sulfolane (tetrahydrothiophene 1,1-dioxide) and its derivatives, methyl-2-sulfonyl ether, N-aryl- 3-sulfonylamine, 2-sulfonyl acetate, dimethyisulfoxide, N-methyl pyrrolidone and the like. Combining two or more of these solvents, particularly the low-molecular-weight polyalkylene glycols, can provide mixed extraction solvents having desirable properties.

Solvent-extraction conditions for aromatics recovery generally are well known to those trained in the art and vary depending on the particular aromatic-selective solvent utilized. Conventional conditions include an elevated temperature and a sufficiently elevated pressure to maintain the solvent reflux to the zone and the heavy reformate feed in the liquid phase. When using a solvent such as sulfolane, suitable temperatures are about 25° to 200° C., preferably about 80° to 150° C., and suitable pressures are about atmospheric to 30 atmospheres gauge and preferably about 3 to 10 atmospheres. Solvent quantities should be sufficient to dissolve substantially all of the aromatic hydrocarbons present in the heavy reformate feed to the extraction zone, and solvent-to-feed ratios by volume of about 2:1 to 10:1 are preferred. Heavier non-aromatic hydrocarbons are displaced from the extract phase at the lower end of the extraction zone by utilizing the known technique of recycling hydrocarbons from the overhead of the stripping column as reflux to the extraction zone, and an aromatic concentrate is recovered from the solvent by distillation.

The aromatics concentrate preferably is partitioned by conventional fractional distillation methods to separate an aromatic compound for subsequent hydroxylation. Benzene may be separated by fractionation from byproduct toluene and $C_8$ and heavier aromatics, for example, with the benzene being sent to phenol production and the toluene and $C_8$ aromatics being used in other chemical syntheses. Toluene and/or heavier aromatics may be processed by conventional hydrodealkylation or disproportionation to yield additional benzene as feed to the hydroxylation step. Alternatively, such toluene and/or heavier aromatics (including bicyclic and polycyclic aromatics) may be fed to the hydroxylation unit for the production of the corresponding substituted hydroxylaromatic compounds.

If desired, another intermediate processing zone could be added to the process combination for conversion of the aromatic compound into other moieties such as heteroatom-substituted intermediates, which in turn could be fed to the hydroxylation zone to obtain the corresponding substituted hydroxylaromatic compounds. For instance, chlorination of benzene to monochlorobenzene or dichlorobenzene could be followed by hydroxylation to such compounds as chlorophenol and dichlorophenol.

Peroxides which are useful for the hydroxylation step of the present invention encompass any of those which are effective to hydroxylate an aromatic nucleus and may be produced using molecular hydrogen as a feedstock. Hydrogen peroxide is especially preferred, although organic peroxides such as percarboxylic acids and alkyl hydroperoxides may be suitable. Hydrogen peroxide can be produced by direct combination of molecular hydrogen and oxygen or by reaction of molecular oxygen with various hydrogen-containing compounds. The preferred process to produce hydrogen peroxide in the context of the present invention is based on a reaction cycle comprising autoxidation of 2-alkylanthrahydroquinones. An alkylanthraquinone in solution is catalytically hydrogenated to its corresponding alkylanthrahydroquinone, which subsequently is aerated with an oxygen-containing gas to form hydrogen peroxide and regenerate the alkylanthroquinone. The 2-alkyl-anthrahydroquinone, i.e., 2-alkyl-9,10-anthracenediol or 2-alkylanthraquinol, generally is designated as the reaction carrier, hydrogen carrier or working material. The solvent for the reactants is called the working solution, and may comprise one or more of alcohols, esters, caprolactams, ureas, amides and pyrollidones. The reaction carrier preferably is hydrogenated over a palladium catalyst which forms a complex with the carrier.

Favored industrial 2-anthraquinone carriers include 2-tert-amylanthraquinone, 2-iso-sec-amylanthraquinone, 2-tert-butylanthraquinone and 2-ethylanthraquinone. During hydrogenation of the alkylanthraquinone to its corresponding alkylanthrohydroquinone, the latter may undergo further reduction to a tetrahydroalkylanthrahydroquinone. This compound releases hydrogen peroxide with the formation of a tetrahydroalkylanthraquinone, which can react with the alkylanthrahydroquinone to reform alkylanthraquinone plus tetrahydroalkylanthrahydroquinone, i.e., effect a parallel reaction sequence. This latter sequence is a slower reaction, requiring higher temperatures, which is significant in some commercial processes. Various byproducts of the reactions build up in the working solution until purged.

The preferred palladium catalyst used in the hydrogenation reaction may be supported on a carrier as a slurry or fixed bed or used as palladium black, wire screen or gauze. Slurry catalysts may be removed and rejuvenated or replaced without a shutdown, but is burdened with suspension difficulties. A fixed catalyst bed requires less stringent feed filtration and avoids inflexibility associated with maintenance of suspension, but requires periodic shutdowns for catalyst rejuvenation or replacement. Hydrogenation operating conditions include a pressure of from about 0.2 to 0.5 MPa absolute and a temperature of up to about 75° C. Minimization of the tetrahydroalkylanthraquinone reaction sequence is favored by lower temperatures in about the 25° to 40° C. range.

Other considerations in the production of hydrogen peroxide are outlined in, e.g., Kirk Othmer Encyclopedia of Chemical Technology Rev. 4, Vol. 13, pages 966–981.

Hydrogen peroxide is the preferred peroxide to use in the practice of this invention, but other peroxides also may be used in appropriate circumstances. For example, if a completely homogeneous reaction mixture is required without the use of a solvent then an organic peroxide may be used instead of hydrogen peroxide: examples include peroxycarboxylic acids, alkyl hydroperoxides and dialkylperoxides. The preferred hydrogen peroxide is used as an aqueous solutions; costly 38 mass-% solutions have been the standard in the past, but more recent technology permits dilute solutions of less than 10 mass-% or even about 5 mass-% aqueous hydrogen peroxide solutions. As to the relative amounts of hydrogen peroxide and aromatic compound, at a high efficiency of peroxide utilization approximately equal molar amounts of hydrogen peroxide and the aromatic compound are preferable. In the most usual case, from about 0.9 to about 1.1 molar proportions of hydrogen peroxide are used per mole of aromatic compound. However, where one component is much more expensive than the other, the molar proportions of hydrogen peroxide to aromatic compound may vary between about 0.5 and 2, or even between about 0.2 and about 5.

One or more of a range of aromatic compounds from the aromatization and aromatics-recovery zones may be hydroxylated in the practice of this invention. Preferably the aromatic compound comprises benzene or one or more alkylbenzenes such as toluene or xylenes. Production of phenol from benzene is especially preferred, with cresols from toluene and xylenols from xylenes also being favored. A commercially feasible process would feature a high conversion of the aromatic compound, generally above about 80%, and particularly a high selectivity to the hydroxy aromatic, e.g., phenol.

The use of solvents to increase miscibility and to provide at least microhomogeneity with respect to hydrogen peroxide and the aromatic compound has an important beneficial effect. The purpose of the solvent is to solubilize, at least in part, both the aromatic compound and hydrogen peroxide without significantly decreasing the utilization efficiency of hydrogen peroxide and without being itself involved in a chemical reaction its nature is unimportant. One or more of methanol, ethanol, isopropyl alcohol, acetone, methyl ethyl ketone, acetic acid, acetonitrile and water may be employed as solvents. More generally, alcohols and ketones from 1–4 carbon atoms, nitriles with up to 5 carbons, and carboxylic acids having up to about 6 atoms are suitable. An alternative means of promoting contact between the aromatic compound and hydrogen peroxide is to use a phase transfer agent to effect the transfer of hydrogen peroxide into the phase with the aromatic compound, or the transfer of the aromatic compound into the aqueous phase of hydrogen peroxide. Yet another means of achieving the same result to conduct the reaction in the presence of a surfactant which in effect acts as a phase transfer agent by forming emulsions or microemulsions.

The hydroxylation may be practiced either in a batch or in a continuous mode. In a batch reaction catalyst preferably is used in an amount anywhere from about 5 up to perhaps 40 mass-% based on the aromatic substrate to be hydroxylated with reaction times of up to about 24 hours. Hydroxylation also may be effected in a continuous mode by passing a mixture of the reactants over a fixed bed of the hydroxylation catalyst; the use of a homogeneous feedstock is advantageous in ensuring adequate contact between the hydrogen peroxide and the aromatic substrate in a fixed-bed operation. Provided that the mutual relative miscibility of the aromatic compound and the aqueous solution of hydrogen peroxide is limited, a solubilizing agent may be used to ensure the formation of a single homogeneous liquid phase. Suitable solubilizing agents are selected from families of organic compounds comprising but not limited to alcohols (including polyhydric alcohols), ethers, ketones, nitriles, etc., in general exhibiting suitably high solubility in both the organic and aqueous phases; an especially preferred solubilizing agent is acetone. Reaction temperatures are between 0° and 100° C., preferably between about 10 and 60° C., and most preferably at as low a temperature within this range as is consistent with an acceptable reaction rate.

Any suitable catalyst as known in the art may be used for hydroxylation as embodied in the present process combination. The use of a variety of molecular sieves have been disclosed as suitable catalysts, as well as halides alone or in combination with, e.g., carbon dioxide. A favored catalyst comprises titanium-containing silicalites as disclosed in U.S. Pat. No. 4,410,501, incorporated herein by reference.

An especially preferred catalyst to convert benzene to phenol in virtually quantitative yields and with virtually 100% efficiency in utilization of hydrogen peroxide is a titano-aluminosilicate composition as taught in U.S. Pat. Nos. 5,098,687 and 5,233,097, both incorporated herein by reference. Such crystalline molecular-sieve compositions are those having a three-dimensional microporous framework structure of $AlO_2$, $SiO_2$ and $TiO_2$ tetrahedral oxide units with a unit empirical formula on an anhydrous basis of $(Ti_xAl_ySi_z)O_2$, where y represents the atom fraction of aluminum in the framework and is at least 0.02, where x represents the atom fraction of titanium in the framework and is at least 0.02, and where z represents the atom fraction of silicon in the framework and is at least 0.5. More typically, the value of each of x and y will be between about 0.02 and about 0.48, z will range from 0.50 to 0.96, and x+y+z=1.0. A particularly desirable variant is one where the molecular sieve has its exchangeable hydrogen ions replaced by one of the alkali metal or alkaline earth metal cations.

Representatives of the crystalline aluminosilicate zeolite molecular sieves which may be employed to afford the titanoaluminosilicate catalysts of this invention include, but are not limited to, erionite, mordenite, clinoptilolite, zeolite Y, zeolite L, zeolite LZ-105, zeolite omega, zeolite beta, zeolite TMA offretite, zeolite ZSM-5, zeolite ZSM-34, zeolite ZSM-35, and zeolite LZ-202. Both naturally occurring and synthetically prepared zeolite molecular sieves can be used. Zeolite Y is disclosed in U.S. Pat. No. 3,130,007; zeolite L is disclosed in U.S. Pat. No. 3,216,789; zeolite LZ-105 is disclosed in U.S. Pat. No. 4,257,885; zeolite omega is disclosed in U.S. Pat. No. 4,241,036; zeolite beta is disclosed in U.S. Pat. No. 3,308,069; zeolite ZSM-5 is disclosed in U.S. Pat. No. 3,702,886; and ZSM-34 is disclosed in U.S. Pat. No. 4,086,186; and zeolite ZSM-35 is disclosed in U.S. Pat. No. 3,992,466. Examples of the titanoaluminosilicate molecular sieves include those molecular sieves having the crystal structure selected from the group consisting of erionite, mordenite, clinoptilite, zeolite Y, zeolite Ω, zeolite β, zeolite TMA offretite, zeolite ZSM-5, zeolite ZSM-34, zeolite ZSM-35, zeolite LZ-202, and zeolite LZ-105. Particularly favored in the practice of our invention are the titanium aluminosilicates based on LZ-105 and ZSM-5.

EXAMPLES

The following examples are presented to demonstrate the present invention and to illustrate certain specific embodiments thereof. These examples should not be construed to limit the scope of the invention as set forth in the claims. There are many possible other variations, as the skilled routineer will recognize, which are within the spirit of the invention.

Example I

The oxidation of benzene by hydroperoxide in the presence of various catalysts was studied under standard conditions (ambient temperature [ca. 20° C.], 24 hours, equimolar quantities of benzene, hydrogen peroxide (30%), and phenol dissolved in acetone (50% solution), 40 mass-% catalyst based on benzene). Both inactivated catalyst and activated potassium ion-exchanged catalyst were tested. Activation was performed by flowing hydrogen over the catalyst at 550° C. for 14 hours. Total yield of phenol is the product of conversion and selectivity, i.e., percent yield=(percent conversion)×(percent selectivity)/100.

| CATALYST | INACTIVATED | | POTASSIUM ION EXCHANGE* | |
|---|---|---|---|---|
| | CON-VERSION | SELEC-TIVITY | CON-VERSION | SELEC-TIVITY |
| Ti Mordenite | 26.45 | 80.76 | 16.48 | 86.91 |
| Ti NH$_4$ Y | 29.36 | 84.86 | 23.76 | 94.35 |
| Ti LZ-202 | 40.70 | 83.5 | 25.01 | 89.85 |
| Ti Beta | 36.89 | 82.68 | 22.42 | 88.11 |
| Ti NH$_4$ L | 60.94 | 95.39 | 39.62 | 96.80 |
| TS-1 | 35.18 | 91.70 | 21.65 | 46.5 |
| Ti LZ-210 | 12.11 | 15.00 | 3.44 | 19.00 |
| Ti ZSM-5 | 89.7 | 99.5 | | |
| Ti LZ-105 | 75.60 | 83.44 | 92.10 | 97.1 |

*and hydrogen activation

The potassium ion-exchanged Ti LZ-105 catalyst was tested in a continuous recirculation reactor. Benzene and H$_2$O$_2$ were combined in a 1:1 molar ratio in a reaction mixture with 21 mass% water and 58.2 mass % acetone, and 100 cc of the mixture was passed over 2 grams of catalyst at ambient temperature and atmospheric pressure for 48 passes with two intermediate reactivations with nitrogen at 550° C.; ultimate benzene conversion was 99.1% with 83.5% selectivity to phenol. Phenol then was added to the above reaction mixture in a 1:1:1 molar ratio with benzene and hydrogen peroxide and the experiment was repeated; benzene conversion after 28 cycles was 99.5% with about 98% selectivity to phenol.

Example II

The process combination of the invention was evaluated to compare its economics with those of conventional technologies. Yields, investment, and operating costs were developed for the combination of aromatization, aromatics recovery, peroxidation and hydroxylation to yield phenol from a paraffinic raffinate stream. The raffinate feedstock had the following characteristics:

| Sp. gr. | 0.6896 |
|---|---|
| ASTM D-86, °C.: | |
| IBP | 70 |
| 10% | 77 |

| | |
|---|---|
| 50% | 86 |
| 50% | 108 |
| EP | 138 |
| Mass % | |
| Paraffins | 90.3 |
| Olefins | 0.1 |
| Naphthenes | 6.8 |
| Aromatics | 2.8 |

Example III

Yields were estimated for the overall process combination based on known yield parameters for each of the process units. In the aromatization zone, benzene, toluene and $C_8$ aromatics are formed from the raffinate plus a small amount of light straight-run naphtha in the aromatization zone and separated into individual products in the aromatics-recovery zone. A portion of the byproduct hydrogen from aromatization is converted to hydrogen peroxide in the peroxidation zone, and reacted with the benzene in the hydroxylation zone to obtain phenol. Yields were calculated as follows for the production of 100,000 metric tons per annum (t/a) of phenol:

| | |
|---|---|
| Raffinate feedstock | 120,550 |
| Light naphtha | 15,700 |
| Oxygen from air (to balance) | 32,320 |
| Total feeds | 168,570 |
| Phenol | 100,000 |
| Toluene | 19,600 |
| $C_8$ aromatics | 17,970 |
| $H_2$-rich gas (92 mole-% $H_2$) | 6,390 |
| Fuel gas | 1,780 |
| Phenol byproducts | 3,590 |
| Water | 19,140 |
| Total products | 168,570 |

Example IV

Investment and operating costs were calculated for the process combination represented by the yield structure in Example III.

Investment costs for production of benzene and hydrogen, peroxidation to yield hydrogen peroxide and hydroxylation of benzene to phenol were based on battery-limits erected costs plus sufficient offsite investment to place the processing units in an existing petrochemical complex. These were estimated as follows in millions of dollars:

| | |
|---|---|
| Aromatization and separation | $50.0 |
| Hydrogen peroxide by peroxidation | 67.5 |
| Phenol by hydroxylation | 49.0 |
| Total investment | $166.5 |

Operating costs include utilities, catalyst and chemical usage and replacement costs, labor, maintenance, overhead, administration, interest on working capital, and depreciation. Utility costs reflect an electric power cost of $0.05/kWh and a fuel cost of $2.15/GJ. Operating costs were calculated as follows in millions of dollars per year:

| | |
|---|---|
| Utilities | $10.56 |
| Catalyst and chemicals | 4.82 |
| Labor, maintenance, overhead, admin. | 12.64 |
| Interest and depreciation | 19.10 |
| Total operating costs | 47.12 |
| Operating costs per ton of phenol | $471.20 |

Example V

Yields and costs were calculated as a control in economic evaluation for a process known in the art, the hydroxylation of purchased benzene to phenol using purchased hydrogen peroxide. Yields are as follows:

| | |
|---|---|
| Benzene feedstock | 84,690 |
| Hydrogen peroxide (100% basis) | 38,040 |
| Total feeds | 122,740 |
| Phenol | 100,000 |
| Phenol byproducts | 3,590 |
| Water | 19,140* |
| Total products | 122,740 |

*plus water and inert solvent present in the feed

Investment cost for the battery-limits plant plus incremental offsites is about $49,000,000. Operating costs are as follows on the same basis as used for the process combination of the invention, in millions of dollars per year:

| | |
|---|---|
| Utilities | $2.72 |
| Catalyst and chemicals | 0.94 |
| Labor, maintenance, overhead, admin. | 5.64 |
| Interest and depreciation | 5.80 |
| Total operating costs | $15.10 |
| Operating costs per ton of phenol | $151.00 |

Example VI

Yields and costs were calculated as a second control for the most widely used commercial process for phenol production, via cumene. Benzene and propylene are reacted to form cumene, which then is oxidized with air to yield cumene hydroperoxide which in turn is cleaved to obtain phenol and acetone.

| Yields are as follows: | |
|---|---|
| Benzene feedstock | 90,030 |
| Propylene | 53,460 |
| Hydrogen (α-methylstyrene sat'n) | 130 |
| Oxygen from air (to balance) | 35,910 |
| Total feeds | 179,530 |
| Phenol | 100,000 |
| Acetone | 61,900 |
| Propane | 2,680 |
| Heavy aromatics | 7,810 |
| Tar | 5,200 |
| Water | 1,940 |
| Total products | 179,530 |

Investment cost for the battery-limits plant plus incremental offsites is about $90,000,000. Operating costs are as follows on the same basis as used for the process combination of the invention, in millions of dollars per year:

| | |
|---|---|
| Utilities | $4.66 |
| Catalyst and chemicals | 1.96 |
| Labor, maintenance, overhead, admin. | 10.89 |
| Interest and depreciation | 10.94 |
| Total operating costs | $28.35 |
| Operating costs per ton of phenol | $283.50 |

EXAMPLE VII

The economics of the process combination of the invention is compared below to the economics of the known processes of Examples V and VI, using reasonable current feedstock and product prices (ton=metric ton). For each of the processes compared, a discounted-cash-flow internal rate of return (DCF-IRR) is calculated. The figures represent millions of dollars per annum unless otherwise designated:

| | Invention | Example V | Example VI |
|---|---|---|---|
| Revenues | | | |
| Phenol @ $772/ton | 77.20 | 77.20 | 77.20 |
| Acetone @ $400/ton | — | — | 24.76 |
| Toluene @ $270/ton | 5.29 | — | — |
| $C_8$ aromatics @ $280/ton | 5.03 | — | — |
| Heavy aromatics @ $175/ton | — | — | 1.37 |
| Propane @ $130/ton | — | — | 0.35 |
| Hydrogen* @ $900/ton | 3.39 | — | — |
| Fuel gas and tar @ $2.15/GJ | 0.48 | — | 0.47 |
| Total revenues | 91.39 | 77.20 | 104.15 |
| Costs | | | |
| Raffinate feedstock @ $150/ton | 18.08 | — | — |
| Benzene @ $350/ton | — | 29.64 | 31.51 |
| Light ends @ $110/ton | 1.73 | — | — |
| Hydrogen peroxide @ $772/ton | — | 29.37 | — |
| Propylene @ $530/ton | — | — | 28.33 |
| Hydrogen @ $900/ton | — | — | 0.12 |
| Operating costs | 47.12 | 15.10 | 29.85 |
| Total costs | 66.93 | 74.11 | 89.81 |
| Margin | 24.46 | 3.09 | 14.34 |
| Investment, $millions | 166.5 | 49.0 | 105.0 |
| Return: DCF-IRR, %/Year** | 21.0% | 10.1% | 19.8% |

*Calculated on quantity of pure hydrogen, contained in 92 mole-% stream
**Based on 10 years' operation, 10%/year depreciation Phenol byproducts and water were not assigned values, as treating costs may compare to product values and the values would not affect the comparison significantly.

Based on the assumed values as indicated, the process combination of the invention shows attractive economics compared to those based on purchased hydrogen peroxide and economics which are comparable to those based on production and peroxidation of cumene. The relative economics are strongly dependent on feedstock and byproduct prices, however. Low-cost benzene would be favorable for both of the known routes to phenol based on Examples V and VI. A low-cost supply of hydrogen peroxide would improve the attractiveness of the Example V approach. A favorable market for byproduct acetone would be of significant benefit to the Example VI route based on cumene. The choice of processing route, therefore, depends to a large extent on the raw-material and market position of each potential phenol producer.

We claim:

1. A process combination for the production of a hydroxylaromatic compound from a mixed hydrocarbon feedstock comprising the steps of:
   (a) contacting the feedstock with an aromatization catalyst in an aromatization zone at reforming conditions to obtain an aromatics-rich effluent stream and a hydrogen concentrate;
   (b) separating the aromatics-rich effluent into an aromatics concentrate and a nonaromatics stream in an aromatics-recovery zone and partitioning the concentrate to obtain an aromatic compound;
   (c) processing the hydrogen concentrate in a peroxidation zone at peroxidation conditions to obtain a peroxide; and,
   (d) hydroxylating the aromatic nucleus of the aromatic compound comprising reacting the aromatic compound with the peroxide in the presence of a hydroxylation catalyst at hydroxylation conditions in a hydroxylation zone to obtain a hydroxylaromatic product.

2. The process combination of claim 1 wherein the aromatic compound is selected from the group consisting of benzene, toluene and xylenes.

3. The process combination of claim 2 wherein the aromatic compound consists essentially of benzene and the hydroxylaromatic compound comprises phenol.

4. The process combination of claim 1 wherein the peroxide is selected from the group consisting of hydrogen peroxide, peroxycarboxylic acids, alkyl hydroperoxides, dialkylperoxides, and peroxydisulfuric acid.

5. The process combination of claim 4 wherein the peroxide is hydrogen peroxide.

6. The process combination of claim 1 wherein the aromatization catalyst of step (a) comprises a platinum-group metal component and a nonacidic large-pore molecular sieve.

7. A process combination for the production of phenol from a hydrocarbon feedstock comprising the steps of:
   (a) contacting the feedstock with an aromatization catalyst in an aromatization zone at reforming conditions to obtain an aromatics-rich effluent stream and a hydrogen concentrate;
   (b) separating the aromatics-rich effluent into an aromatics concentrate and a nonaromatics stream in an aromatics-recovery zone and partitioning the concentrate to obtain benzene;
   (c) processing the hydrogen concentrate in a peroxidation zone at peroxidation conditions to obtain hydrogen peroxide; and,
   (d) hydroxylating the benzene with hydrogen peroxide in the presence of a hydroxylation catalyst at hydroxylation conditions in a hydroxylation zone to obtain phenol.

8. The process combination of claim 7 wherein the hydrocarbon feedstock comprises a naphtha feedstock.

9. The process combination of claim 7 wherein the hydrocarbon feedstock comprises a raffinate from aromatics extraction.

10. The process combination of claim 9 wherein the raffinate comprises nonaromatics recycled from the aromatics-recovery zone.

11. The process combination of claim 7 wherein the aromatization catalyst of step (a) comprises a platinum-group metal component and a nonacidic large-pore molecular sieve.

12. The process combination of claim 11 wherein the platinum-group metal component comprises platinum in an amount of from about 0.01 to 0.2 mass-%.

13. The process combination of claim 11 wherein the nonacidic large-pore molecular sieve comprises potassium-form L-zeolite.

14. The process combination of claim 7 wherein the feedstock comprises $C_2$–$C_6$ aliphatic hydrocarbons and the aromatization catalyst comprises MFI, a gallium component and aluminum phosphate.

15. The process combination of claim 7 further comprising upgrading the hydrogen concentrate to a purified hydrogen stream.

16. The process combination of claim 7 wherein the hydroxylation conditions comprise a temperature of from about 10° to about 60° C.

17. The process combination of claim 7 wherein the hydroxylation catalyst comprises a crystalline titanoaluminosilicate molecular sieve composition wherein the titanium, aluminum, and silicon are present as framework tetrahedral oxide units having a unit empirical formula on an anhydrous basis of $(Ti_xAl_ySi_z)O_2$ wherein each of x and y independently has a value between about 0.02 and about 0.48, z has a value of at least 0.50 up to 0.96, and (x+y+z)=1.

18. The process combination of claim 7 wherein the peroxide and the aromatic compound are reacted in a solvent selected from the group consisting of saturated alcohols having 1 to 4 carbon atoms, saturated ketones having up to 4 carbon atoms, and saturated carboxylic acids with 2 to about 6 carbon atoms.

19. The process combination of claim 7 wherein hydrogen peroxide is used as an aqueous solution containing not more that 10 mass-% hydrogen peroxide.

20. The process combination of claim 7 wherein hydrogen peroxide is present in the hydroxylation zone in a molar proportion of from about 0.2 to about 5 relative to the aromatic compound.

21. A process combination for the production of phenol from a naphtha feedstock comprising the steps of:

(a) contacting the feedstock with an aromatization catalyst comprising a platinum-group metal component and a nonacidic large-pore molecular sieve in an aromatization zone at reforming conditions to obtain an aromatics-rich effluent stream and a hydrogen concentrate;

(b) separating the aromatics-rich effluent into an aromatics concentrate and a nonaromatics stream in an aromatics-recovery zone and partitioning the concentrate to obtain benzene;

(c) processing the hydrogen concentrate in a peroxidation zone at peroxidation conditions to obtain hydrogen peroxide; and, (d) hydroxylating the benzene with hydrogen peroxide in the presence of a hydroxylation catalyst at hydroxylation conditions in a hydroxylation zone to obtain phenol.

\* \* \* \* \*